United States Patent [19]

Loeb et al.

[11] Patent Number: 4,872,464
[45] Date of Patent: Oct. 10, 1989

[54] PUBIC PROPHYLACTIC WITH SNAP-OVER SHIELD

[75] Inventors: Marvin P. Loeb, Huntington Beach, Calif.; John F. Perry, Vernon Hills, Ill.

[73] Assignee: Xtramedics, Inc., Deerfield, Ill.

[21] Appl. No.: 81,360

[22] Filed: Aug. 4, 1987

[51] Int. Cl.$^4$ .............................................. A61F 5/44
[52] U.S. Cl. ...................................... 128/844; 604/352
[58] Field of Search .................. 128/132 R, 830, 842, 128/844, 79, 845, 883; 604/317, 327, 332, 337–339, 342–345, 347–353, 355, 346

[56] References Cited

U.S. PATENT DOCUMENTS

| | | | |
|---|---|---|---|
| 2,305,453 | 12/1942 | Martos | 604/346 X |
| 2,591,783 | 4/1952 | Craddock | 604/353 X |
| 3,677,225 | 7/1972 | Czirely | 604/352 X |
| 3,759,254 | 9/1973 | Clark | 604/349 X |
| 4,664,104 | 5/1987 | Jaicks | 128/132 R |
| 4,794,920 | 1/1989 | Robichaud | 128/844 |

FOREIGN PATENT DOCUMENTS

| | | | |
|---|---|---|---|
| 1158507 | 12/1983 | Canada | 604/349 |
| 0220962 | 5/1987 | European Pat. Off. | 604/349 |
| 1595711 | 8/1981 | United Kingdom | 604/349 |
| 2075847 | 11/1981 | United Kingdom | 604/349 |

*Primary Examiner*—C. Fred Rosenbaum
*Assistant Examiner*—Mario Costantino

[57] ABSTRACT

A pubic shield is provided having an elastic tubular sheet attached to a substantially frusto-conical structure at the relatively smaller diameter of the frusto-conical structure. The frusto-conical structure forms a shield member having substantially two stable positions, a storage position and a use position. The shield member is in the use position when the tubular sheet extends away from the frusto-conical member. Use of the pubic shield, alone or with a bioadhesive, provides an enhanced prophylactic effect over that of a typical condom.

14 Claims, 3 Drawing Sheets

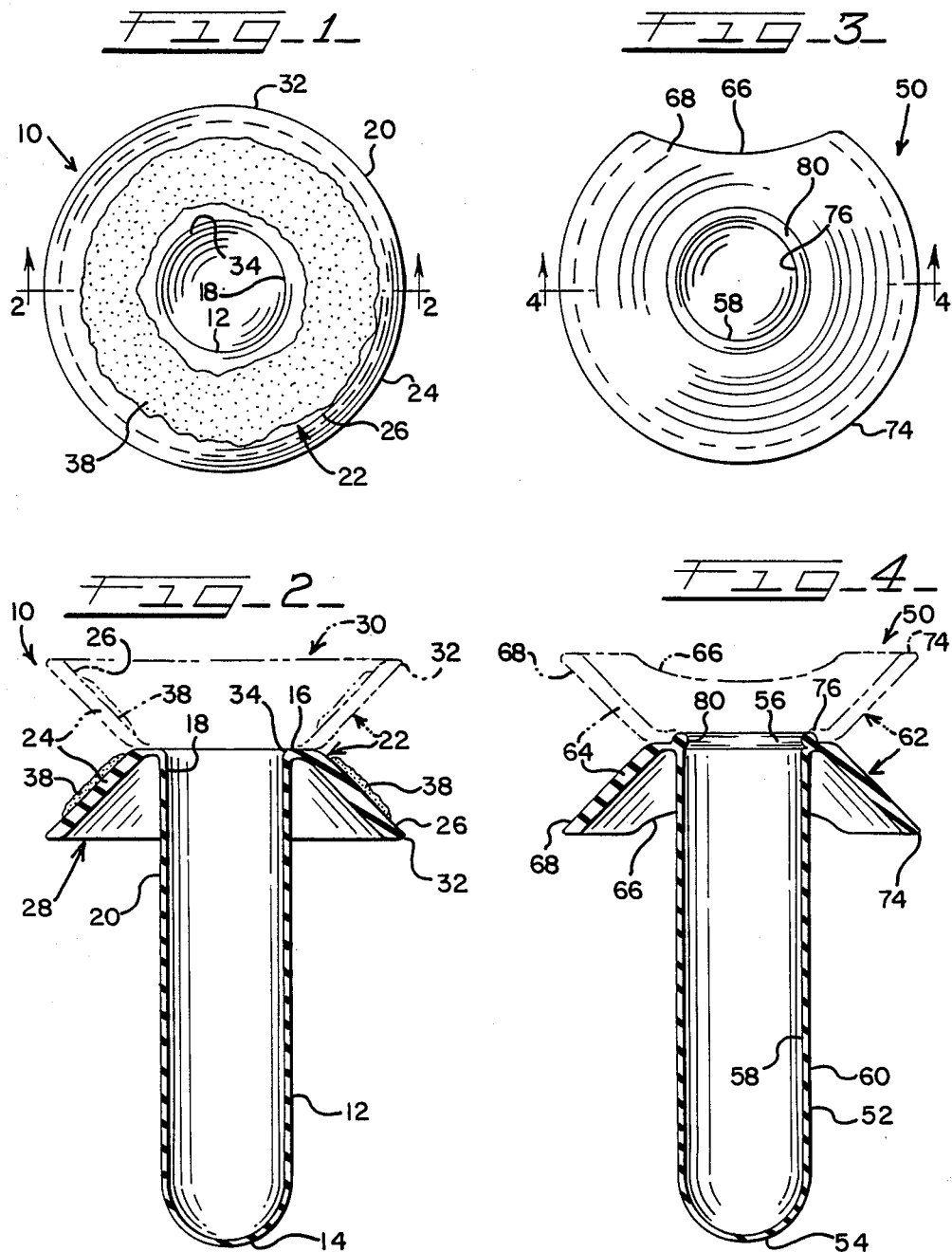

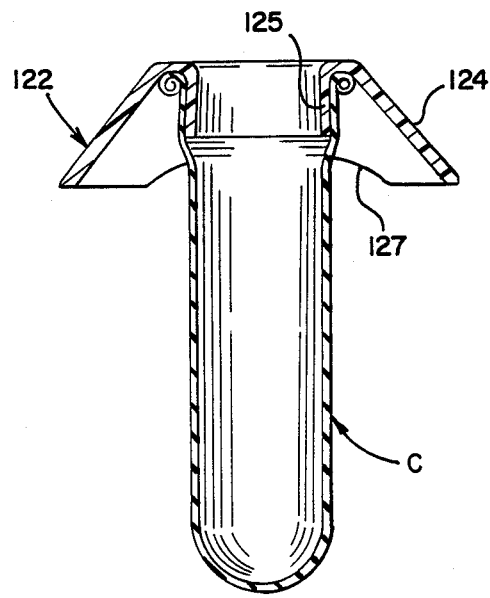
FIG_5_
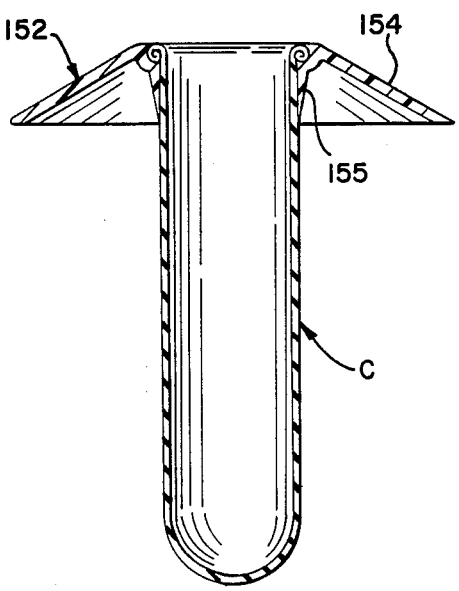
FIG_8_
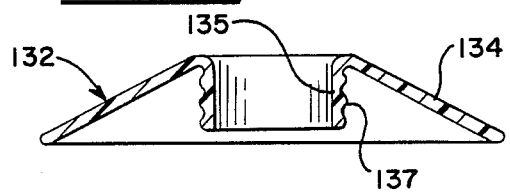
FIG_6_
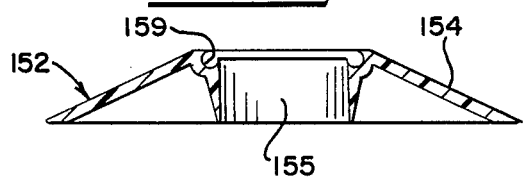
FIG_9_
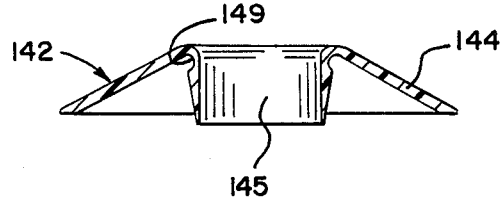
FIG_7_

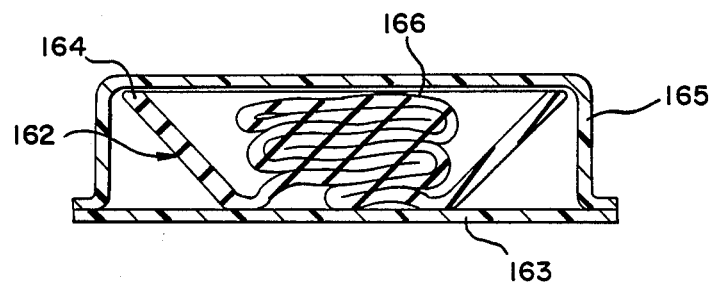
FIG_10_
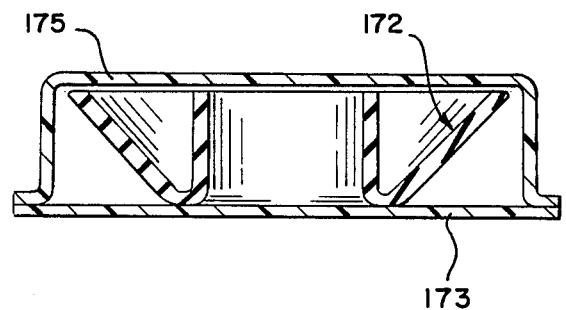
FIG_11_

PUBIC PROPHYLACTIC WITH SNAP-OVER SHIELD

FIELD OF THE INVENTION

The present invention pertains to hygienic appliances, and more particularly to male contraceptive and prophylactic devices.

BACKGROUND OF THE INVENTION

The incidence of venereal disease is increasing at an alarming rate. The number of people infected each year with all types of venereal disease is rising. The newest, and most deadly, sexually transmitted disease, acquired immune deficiency syndrome (AIDS), has only been discovered within the last decade. With respect to this particular disease, there has been a growing awareness of the potential for transmitting the virus responsible for inducing AIDS through minor skin abrasions. It has also been shown that this virus is present in vaginal fluids. Thus, while the use of a conventional condom decreases the likelihood of contracting AIDS or other sexually transmitted diseases, a more effective prophylactic would be desirable.

Because of the role the condom plays in prevention of venereal disease, a heightened interest has developed in the configuration of the condom itself. While prior developments had centered on durability and material variations, see, for example U.S. Pat. No. 4,406,853 to Miyata and 4,527,988 to Lutz et al., the configuration of the condom itself is now undergoing scrutiny.

Problems associated with the use of condoms include: slippage, allowing some body fluids to leak in or out; tearing while donning or removing; and insufficient protection of the pubic region from exposure to body fluids that may contain an AIDS-inducing virus.

The present invention contemplates a device that provides enhanced prophylactic benefits to an external, male-worn, contraceptive device, is comfortable to wear, and easy to don and remove.

SUMMARY OF THE INVENTION

The present invention provides a pubic shield that extends over the pubic region and comprises a shield member in combination with an elastic tubular sheet having an inner surface, an outer surface, an open proximal end, and a closed distal end. The shield member includes an outwardly extending flexible flange or shield about the periphery of the tubular sheet at the proximal end thereof. The shield member is a hollow, self-supporting, resilient, substantially frusto-conical structure joined about its relatively smaller diameter to the elastic tubular sheet at the proximal end thereof. The shield member also defines a contact face that can be provided with a bioadhesive, if desired.

The snap-over pubic shield of this invention is positionable in two stable configurations, a storage position and a use position. The storage position is one in which the tubular sheet can be collapsed within the cavity defined by the hollow frusto-conical structure. The use position is one in which the tubular sheet extends away from the hollow frusto-conical structure. The configuration of the shield is such that it only has these two stable positions. The shield, in its use position, enhances the prophylactic properties of a condom and in its storage position provides for compact packaging of the device.

The snap-over shield can be unitary with the condom portion or can be a separate element adapted to receive a conventional condom.

A variant of the present invention includes a bioadhesive on the face of the shield contiguous to the user, i.e., the contact face. The bioadhesive can include a biocide such as a germicide, certain antibiotics, an anti-viral agent, a spermicide, and the like.

Another embodiment of the present invention further provides an annular constricting region that aids in maintaining an erection.

Numerous other advantages and features of the invention will become readily apparent from the following detailed description of the invention, the accompanying drawing, and the claims.

BRIEF DESCRIPTION OF THE DRAWING

In the drawing,

FIG. 1 is a top plan view of a snap-over pubic shield with a unitary condom;

FIG. 2 is a cross-sectional elevation taken along plane 2—2 of FIG. 1 and shows the snap-over pubic shield in storage position, with its use position shown in phantom;

FIG. 3 is a top plan view of another embodiment of the snap-over shield in storage position and provided with an annular constricting region and an arcuate cut-out;

FIG. 4 is a cross-sectional elevation taken along plane 4—4 of FIG. 3, showing the snap-over shield in storage position, with its use position shown in phantom;

FIG. 5 is cross-sectional elevation similar to that of FIG. 2 but showing a snap-over pubic shield that is separable from the condom;

FIG. 6 is a cross-sectional elevation of a snap-over shield adapted to receive a conventional condom;

FIG. 7 is a cross-sectional elevation of another variant of the snap-over shield of this invention adapted to receive a conventional condom;

FIG. 8 is a cross-sectional elevation of yet another embodiment of the present pubic shield and constituted by a shield member that is separable from a condom member;

FIG. 9 is a cross-sectional elevation of the shield member shown in FIG. 8;

FIG. 10 is a cross-sectional elevation of a package containing a snap-over pubic shield of this invention; and FIG. 11 is a cross-sectional elevation of a package containing a further embodiment of a snap-over shield of this invention.

DESCRIPTION OF THE PREFERRED EMBODIMENTS

While this invention is susceptible of an embodiment in many different forms, there are shown in the drawings and will be described hereinbelow in detail certain embodiments thereof with the understanding that the present disclosure is to be considered as an exemplification of the principles of the invention and does not limit the invention only to the illustrated embodiments.

Referring to the drawing, FIG. 1 shows an embodiment of the present invention in the form of a shield-condom combination 10 provided with snap-over flexible shield member 22. The condom portion of the present pubic shield 10 is an elastic tubular sheet 12 having an inner surface 18 and an outer surface 20. The tubular sheet 12 has an open proximal end 16 and a closed distal end 14. Flexible shield member 22 is positioned at the proximal end 16, is unitary therewith, and extends outwardly therefrom. The shield member 22 is in the form of a hollow, self-supporting, resilient, substantially frusto-conical member 24 that can be inverted to a stable position shown in phantom in FIG. 2, as will be discussed in detail hereinbelow. The relatively smaller diameter 34 of frusto-conical member 24 joins with the elastic tubular sheet 12 at its proximal end 16. The shield member 22 defines also a contact face 26 that is continuous with the inner surface 18 of the tubular sheet 12. If desired, shield member 22 can be made of an absorbent material, or provided with an outer layer of such a material, e.g., a hydrophilic polyurethane layer, for absorption and retention of body fluids.

The outwardly extending shield 22 member is positionable in two stable configurations, a storage position 28 and a use position 30. The storage position is one in which the tubular sheet 12 can be collapsed within the hollow frusto-conical member 24. The use position 30 is one in which the tubular sheet 12 extends away from the hollow, frusto-conical member 24, and contact face 26 is in the proximity of the pubic region of the wearer.

In order to change the position of the shield member 22, the user snaps over the shield portion by pushing at the rim, i.e. at the larger diameter 32 of the frusto-conical member 24 and towards its smaller diameter 34. As the shield member is pushed into position, the rim is temporarily extended and crosses a plane of maximal extension before the shield member snaps into its other stable position without application of additional force. For example, if shield member 22 is in its storage position 28 and is being pushed to its use position 30, as the large diameter 32 is being pushed toward the small diameter 34 the large diameter passes through an imaginary central plane defined by the condom aperture at proximal end 16. Once this happens, the shield member 22 no longer requires force to push the larger diameter 32 toward the smaller diameter 34. The larger diameter 32 snaps into the use position 30 by virtue of the resiliency of the frusto-conical member 24. This snap-over action is a result of the configuration of shield member 22, as well as its resiliency.

The angle that frusto-conical member 24 forms with the longitudinal axis of condom portion 20 can vary. However, this angle is an acute angle, preferably an angle of about 45 degrees to about 30 degrees with respect to the aforementioned longitudinal axis. The outside diameter of frusto-conical member 24 is preferably about 6 to 8 inches.

FIGS. 3 and 4 show modifications and additional features of the present invention. In particular, FIG. 3 shows a plan view of a snap-over pubic shield 50 having an arcuate cut-out 66 in the shield portion and an annular constricting region 80 at about the juncture of the frusto-conical member 64 with tubular sheet 52.

While pubic shield 50 is substantially the same as pubic shield 10 with respect to construction and manner of use, one additional feature of the shield 50 is an arcuate cut-out 66 provided in the flexible shield portion 62 which provides clearance for the scrotum. However, the arcuate cutout region of the pubic shield can also be covered by a relatively thin membrane dimensioned so as to prevent contact of the user's scrotum with the sex partner. Elastic tubular sheet 52 having an inner surface 58, an outer surface 60, an open proximal end 56, and a closed distal end 54 is joined to the shield portion 62 about the periphery of the tubular sheet 52 at the proximal end 56. The shield portion 62 is in the configuration of a hollow, self-supporting, resilient, substantially frusto-conical member 64. Attachment to the elastic tubular sheet 52 is about its relatively smaller diameter 76. The shield portion 62 defines a contact face 68 that is continuous with the inner surface 58 of the tubular sheet 52.

Yet another feature of the present invention is illustrated in FIGS. 3 and 4. An annular constricting region 80 is shown at the junction of the elastic tubular sheet 52 and the outwardly extending shield portion 62. The annular region 80 projects inwardly from shield portion 62 and is more rigid than either the tubular sheet 52 or the frusto-conical member 64. As will be explained below, the annular region 80 assists in the maintainance of an erection by partially constricting blood flow.

The annular constricting region 80 is positioned so that it is displaced toward the longitudinal axis of the tubular sheet 52 when the shield portion 62 is in the use position. The annular constricting region 80 thereby reduces the opening at the proximal end 56 of the tubular sheet 52 so that pressure is applied to the dorsal vein at the base of the penis to restrict the flow of venal blood back to the body. This action tends to maintain blood in the male's erectile tissues and thereby assist in maintaining an erection.

The snap-over pubic shield of this invention can also be constituted by separable shield portion and condom portion. In such a case, the latter can be a conventional, commercially available condom. Embodiments illustrating separate or separable shield and condom portions are shown in FIGS. 5 through 9.

In particular, FIG. 5 shows snap-over shield member 122 having a frusto-conical member 124, made of an elastomeric material, and a central tubular extension or boss 125 circumscribed by frusto-conical member 124 and adapted to receive and retain a conventional condom C. An arcuate cut-out region 127 is provided in frusto-conical member 124 to accommodate the scrotum. The distal portion of boss 125 is flared radially outwardly to enhance the retention of condom C thereon. When frusto-conical member 124 is snapped over to its use position, boss 125 extends away from it.

FIG. 6 shows a snap-over shield member 132 provided with central boss 135. The frusto-conical skirt portion 134 of shield member 132 is deeper than the longitudinal or axial dimension of boss 135. The outer surface 137 of boss 135 is ribbed for enhanced condom retention, and may be coated with an adhesive to further enhance condom retention.

FIG. 7 shows a snap-over shield member 142 provided with central boss 145 that tapers to a reduced diameter toward its distal end and has an outer peripheral groove 149 at the junction of boss 145 to frusto-conical skirt portion 144. Peripheral groove 149 not only provides a seat for the rolled-up proximal end of a conventional condom but also a hinge means that facilitates the snap-over action of skirt portion 144. In the embodiment shown in FIG. 7, skirt portion 144 is shallower than the longitudinal or axial dimension of boss 145. That is, when the shield member 142 is in its storage position (as shown), boss 145 is circumscribed by but extends beyond skirt portion 144.

Yet another variant of the present invention is illustrated in FIGS. 8 and 9 where snap-over shield member 152 is adapted to be positioned over a conventional condom C so that boss 155 thereof, unitary with skirt portion 154, surrounds the proximal end of condom C. Inner peripheral groove 159 is defined by the proximal end of boss 155 and receives therewithin the rolled up proximal end of condom C. As the skirt portion 154 is snapped over to its use position, the contour of groove 159 closes up somewhat and envelops further the rolled up portion of condom C thereby locking condom C in place. The depth of skirt portion 154 is substantially the same as the longitudinal or axial dimension of boss 155.

Latex is the preferred material of construction for the snap-over pubic shields of this invention. These shields can also be made of other elastomeric materials including those types of elastomers which integrally contain a spermicide or germicide. Materials of the latter type are illustrated in U.S. Pat. No. 4,589,880 to Dunn et al. Materials of the construction derived from natural sources such as those described in U.S. Pat. No. 4,406,853 to Miyata can be used as well for the condom portion of the present shields.

The present shields also provide a convenient means for grasping the device when donning or removing. Compared to a conventional condom, improved manipulation is gained, resulting in a reduced likelihood of tearing, leaking or spilling.

The present pubic shields can include a bioadhesive for enhanced securement. In pubic shield 10, the bioadhesive 38 is provided on the contact face 26. Similarly, pubic shield device 50 can be provided with a bioadhesive on contact face 68.

A number of bioadhesive compositions are available for this purpose. Illustrative bioadhesives are chemical compounds that adhere to human skin or mucus membranes and that have long been used with buccal compositions or to attach dentures to the mucus membranes of the gums. Bioadhesives are available in many forms, the preferred form being a gel type. An illustrative example is sodium carboxymethylcellulose (NaCMC) dispersed in a polyethylene/mineral oil gel base. Suitable other bioadhesives are described in Gurny et al., Biomaterials 5:336–340 (November, 1984); Ch'ng et al., J. Pharm. Sci. 74 (4): 399–405 (April 1985); and Hui et al., Int. J. Pharmaceutics 26:203–213 (1985).

The bioadhesives can include a biocide, thereby increasing further protection provided by the pubic shields of this invention. Illustrative biocides are germicides, antibiotics, anti-viral agents, spermicides and the like. Bacteriostatic agents also can be used.

Snap-over pubic shields of the present invention packaged in a sealed envelope are illustrated in FIGS. 10 and 11. In FIG. 10, a snap-over pubic shield 162 is positioned on a substantially planar base 163 and covered by a contoured cover 165 removably secured to base 163. Condom portion 116 is in a collapsed state and is received within a cavity defined by skirt portion 164.

In FIG. 11, snap-over pubic shield 172 is positioned on a substantially planar base 173 and enveloped by contoured cover member 175 which, in turn, is removably secured to base 173.

The snap-over pubic shields can be packaged dry or together with a lubricant such as a medical grade silicone lubricant, spermicide or the like.

The foregoing detailed description of the invention and the described embodiments thereof are illustrative. Numerous variations and modifications thereof may be effected without departing from the true spirit and scope of the concepts or principles of this invention.

We claim:

1. An improved condom having a two-position public pubic area shield comprising:

an elastic, elongated tubular penis enclosing member having a longitudinal axis, an inner surface, an outer surface, an open proximal end, and a closed distal end;
   a generally frusto-conically configured, self-supporting, resilient pubic area shield member having opposed first and second side surfaces and a central aperture defined therein whose diameter approximates the diameter of said proximal end, and having a peripheral rim in radially and diagonally outwardly spaced relationship to said aperture;
   annular flexible joining means interconnecting said proximal end with said shield member circumferentially about said aperture whereby said first surface is generally coextensive with said outer surface, and said second surface is generally coextensive with said inner surface;
   said shield member being longitudinally invertable about said annular joining means from a first stable configuration to a second stable configuration;
   said first configuration corresponding to a storage configuration wherein said tubular member, when longitudinally collapsed, is generally nestably receivable with said shield means;
   said second configuration corresponding to a use configuration wherein said tubular member, when extended, projects away from said shield member; and
   said second surface being provided with a bioadhesive.

2. The condom of claim 1 wherein said bioadhesive includes a biocide.

3. The condom of claim 2 wherein said annular joining means is more rigid than said tubular member and said shield member and is positioned so that said annular joining means is displaced toward said longitudinal axis when said shield member is in said use configuration.

4. The condom of claim 1 wherein said shield member is provided with an arcuate cut-out in said rim.

5. The condom of claim 1 contained in a sealed envelope.

6. A snap-over, two-position pubic area shield comprising:

a generally frusto-conically configured self-supporting, resilient pubic area shield member having opposed side surfaces and a central aperture defined therein with aperture edge portions, and having a peripheral rim in radially and diagonally outwardly spaced relationship to said aperture,
   a penis-receiving tubular boss having an inner surface, an outer surface, an open proximal end, and an open distal end,
   said proximal end being circumferentially integrally formed with said aperture edge portions,
   said shield member being invertable about said aperture edge portions from a first stable configuration to a second stable configuration,
   said first configuration corresponding to a storage configuration wherein said tubular boss is circumscribed by said shield member,
   said second configuration corresponding to a use configuration wherein said tubular boss projects away from said shield member.

7. The snap-over pubic shield in accordance with claim 6 contained in a sealed envelope.

8. The snap-over pubic shield in accordance with claim 6 wherein said frusto-conical shield member is provided with an arcuate cut-out in said rim.

9. The snap-over pubic shield in accordance with claim 6 wherein said tubular boss is provided with a ribbed said outer surface.

10. The snap-over pubic shield in accordance with claim 9 wherein an adhesive is present on said ribbed surface.

11. The snap-over pubic shield in accordance with claim 6 wherein said tubular boss is provided with a reduced diameter at said distal end thereof.

12. The snap-over pubic shield in accordance with claim 6 wherein said tubular boss has an outwardly flared said distal end.

13. The snap-over pubic shield in accordance with claim 6 wherein said tubular boss defines an outer peripheral groove at said proximal end thereof.

14. The snap-over pubic shield in accordance with claim 6 wherein said tubular boss defines an inner peripheral groove at said proximal end thereof.

* * * * *